United States Patent
Goodnow, II et al.

(10) Patent No.: US 9,697,337 B2
(45) Date of Patent: Jul. 4, 2017

(54) SYSTEMS AND METHODS FOR MANAGING BLOOD DONATIONS

(75) Inventors: James E. Goodnow, II, Grass Valley, CA (US); James A. Bancroft, Grass Valley, CA (US); Jonathan G. Morgan, San Francisco, CA (US)

(73) Assignee: APPLIED SCIENCE, INC., Grass Valley, CA (US)

( * ) Notice: Subject to any disclaimer, the term of this patent is extended or adjusted under 35 U.S.C. 154(b) by 1061 days.

(21) Appl. No.: 13/445,274

(22) Filed: Apr. 12, 2012

(65) Prior Publication Data

US 2012/0265099 A1    Oct. 18, 2012

Related U.S. Application Data

(60) Provisional application No. 61/474,679, filed on Apr. 12, 2011.

(51) Int. Cl.
*G06F 9/44* (2006.01)
*A61B 5/15* (2006.01)
(Continued)

(52) U.S. Cl.
CPC ........ *G06F 19/366* (2013.01); *A61B 5/15003* (2013.01); *A61B 5/153* (2013.01);
(Continued)

(58) Field of Classification Search
CPC ...... A61B 2560/0209; A61B 5/150389; A61B 5/150229; A61B 5/150946; G06F 19/3412; G06F 19/366
(Continued)

(56) References Cited

U.S. PATENT DOCUMENTS 4,377,852 A   3/1983 Thompson
4,451,158 A   5/1984 Selwyn et al.
(Continued)

FOREIGN PATENT DOCUMENTS

CN   1348740 A   5/2002
CN   1503954 A   6/2004
(Continued)

OTHER PUBLICATIONS

Goodnow et al.; U.S. Appl. No. 14/482,884 entitled "Systems and methods for documenting a blood donation collection process," filed Sep. 10, 2014.
(Continued)

*Primary Examiner* — Sean Dougherty
*Assistant Examiner* — Patrick Fernandes
(74) *Attorney, Agent, or Firm* — Shay Glenn LLP (57) ABSTRACT

Methods and apparatus collecting blood from patients and managing blood donations are provided, which may include any number of features. One feature is a blood collection device configured to collect blood from a patient and periodically transmit blood collection data from the device to a control system. Another feature is a system and method for updating firmware on a plurality of blood collection devices. In one embodiment, a software interface with a blood collection control can be used to specify a blood collection protocol, and the blood collection protocol can be then transmitted to one or more blood collection devices.

7 Claims, 7 Drawing Sheets

| Network Status | Recent Draws | System Utility | Release Data | Options | Hide Display |

| ID | Stat | Flow | ml | Target | Time | Error | Donation ID | Batt | Calibration | Radio |
|---|---|---|---|---|---|---|---|---|---|---|
| Scale 10 | Mid-Draw | 6 | 325 | 470 | 06:25 | - - - | G1234983546 | 66% | 28-Feb, 08:34 | 70% |
| Scale 24 | Inactive | 0 | 0 | 470 | 0:00 | - - - | | 100% | 28-Feb, 08:35 | 65% |
| Scale 52 | End-Recovery | 0 | 474 | 470 | 08:45 | Low Flow | G1234996745 | 66% | 28-Feb, 08:36 | 75% |
| Scale 07 | Inactive | 0 | 0 | 470 | 0:00 | - - - | | 33% | 28-Feb, 08:37 | 65% |
| Scale 63 | Inactive | 0 | 0 | 470 | 0:00 | - - - | | 33% | 28-Feb, 08:39 | 65% |
| Scale 53 | Inactive | 0 | 0 | 470 | 0:00 | - - - | | 100% | 28-Feb, 08:42 | 65% |
| Scale 15 | Inactive | 0 | 0 | 470 | 0:00 | - - - | | 100% | 28-Feb, 08:45 | 65% |
| Scale 22 | Start-Scan | 0 | 0 | 470 | 0:00 | - - - | G1234678594 | 66% | 28-Feb, 08:50 | 65% |
| Scale 33 | Inactive | 0 | 0 | 470 | 0:00 | - - - | | 66% | 28-Feb, 08:51 | 65% |
| Scale 65 | Inactive | 0 | 0 | 470 | 0:00 | - - - | | 100% | 28-Feb, 08:52 | 65% |

(51) Int. Cl.
  *G06F 15/16*   (2006.01)
  *G06F 17/40*   (2006.01)
  *G06F 19/00*   (2011.01)
  *A61B 5/153*   (2006.01)
  *A61B 5/155*   (2006.01)
  *A61B 5/157*   (2006.01)
  *G06F 9/445*   (2006.01)

(52) U.S. Cl.
  CPC ........ *A61B 5/155* (2013.01); *A61B 5/150221* (2013.01); *A61B 5/150229* (2013.01); *A61B 5/150366* (2013.01); *A61B 5/150389* (2013.01); *A61B 5/150755* (2013.01); *A61B 5/150786* (2013.01); *A61B 5/150862* (2013.01); *A61B 5/150946* (2013.01); *G06F 19/3412* (2013.01); *A61B 5/157* (2013.01); *A61B 2560/0209* (2013.01); *G06F 8/665* (2013.01)

(58) Field of Classification Search
  USPC .......................................................... 600/573
  See application file for complete search history.

(56) References Cited

U.S. PATENT DOCUMENTS

| | | |
|---|---|---|
| RE33,924 E | 5/1992 | Valeri |
| 5,403,279 A | 4/1995 | Inaba et al. |
| 5,403,304 A | 4/1995 | Ishida |
| 5,611,048 A | 3/1997 | Jacobs et al. |
| 5,658,240 A | 8/1997 | Urdahl et al. |
| 5,666,500 A | 9/1997 | Roberson |
| 5,845,289 A | 12/1998 | Baumeister et al. |
| 5,857,194 A | 1/1999 | Kelliher et al. |
| 5,912,669 A | 6/1999 | Hsia |
| 5,973,665 A | 10/1999 | Davie et al. |
| 6,008,811 A | 12/1999 | McMillan |
| 6,014,702 A | 1/2000 | King et al. |
| 6,026,684 A | 2/2000 | Calder |
| 6,049,832 A | 4/2000 | Brim et al. |
| 6,113,554 A | 9/2000 | Gilcher et al. |
| 6,131,510 A | 10/2000 | Gasquez |
| 6,216,164 B1 | 4/2001 | Zaremba |
| 6,233,525 B1 | 5/2001 | Langley et al. |
| 6,252,591 B1 | 6/2001 | Dockweiler et al. |
| 6,256,643 B1 | 7/2001 | Cork et al. |
| 6,259,447 B1 | 7/2001 | Kanetake et al. |
| 6,289,382 B1 | 9/2001 | Bowman-Amuah |
| 6,327,624 B1 | 12/2001 | Mathewson et al. |
| 6,332,163 B1 | 12/2001 | Bowman-Amuah |
| 6,334,144 B1 | 12/2001 | Horwitz |
| 6,339,832 B1 | 1/2002 | Bowman-Amuah |
| 6,342,905 B1 | 1/2002 | Diedrich et al. |
| 6,366,658 B1 | 4/2002 | Bjornberg et al. |
| 6,381,654 B1 | 4/2002 | Brawn et al. |
| 6,402,702 B1 | 6/2002 | Gilcher et al. |
| 6,405,924 B1 * | 6/2002 | Shah ...................... 235/462.08 |
| 6,406,919 B1 | 6/2002 | Tyrrell |
| 6,434,568 B1 | 8/2002 | Bowman Amuah |
| 6,434,628 B1 | 8/2002 | Bowman Amuah |
| 6,438,594 B1 | 8/2002 | Bowman Amuah |
| 6,442,748 B1 | 8/2002 | Bowman Amuah |
| 6,446,110 B1 | 9/2002 | Lection et al. |
| 6,453,356 B1 | 9/2002 | Sheard et al. |
| 6,477,580 B1 | 11/2002 | Bowman Amuah |
| 6,477,665 B1 | 11/2002 | Bowman Amuah |
| 6,480,895 B1 | 11/2002 | Gray et al. |
| 6,496,850 B1 | 12/2002 | Bowman Amuah |
| 6,502,213 B1 | 12/2002 | Bowman Amuah |
| 6,508,778 B1 | 1/2003 | Verkaart et al. |
| 6,511,439 B1 | 1/2003 | Tabata et al. |
| 6,519,605 B1 | 2/2003 | Gilgen et al. |
| 6,529,909 B1 | 3/2003 | Bowman Amuah |
| 6,529,948 B1 | 3/2003 | Bowman Amuah |
| 6,539,396 B1 | 3/2003 | Bowman Amuah |
| 6,549,949 B1 | 4/2003 | Bowman Amuah |
| 6,550,057 B1 | 4/2003 | Bowman Amuah |
| 6,571,282 B1 | 5/2003 | Bowman Amuah |
| 6,578,068 B1 | 6/2003 | Bowman Amuah |
| 6,582,386 B2 | 6/2003 | Min et al. |
| 6,601,192 B1 | 7/2003 | Bowman Amuah |
| 6,601,234 B1 | 7/2003 | Bowman Amuah |
| 6,606,660 B1 | 8/2003 | Bowman Amuah |
| 6,611,806 B1 | 8/2003 | Harvey |
| 6,615,199 B1 | 9/2003 | Bowman Amuah |
| 6,615,253 B1 | 9/2003 | Bowman Amuah |
| 6,622,176 B2 | 9/2003 | Jones et al. |
| 6,636,242 B2 | 10/2003 | Bowman Amuah |
| 6,640,238 B1 | 10/2003 | Bowman Amuah |
| 6,640,244 B1 | 10/2003 | Bowman Amuah |
| 6,640,249 B1 | 10/2003 | Bowman Amuah |
| 6,641,552 B1 | 11/2003 | Kingsley et al. |
| 6,665,868 B1 | 12/2003 | Knowles et al. |
| 6,673,314 B1 | 1/2004 | Burbank et al. |
| 6,714,945 B1 | 3/2004 | Foote et al. |
| 6,715,145 B1 | 3/2004 | Bowman Amuah |
| 6,718,334 B1 | 4/2004 | Han |
| 6,730,054 B2 | 5/2004 | Pierce et al. |
| 6,742,015 B1 | 5/2004 | Bowman Amuah |
| 6,773,413 B2 | 8/2004 | Keller et al. |
| 6,808,503 B2 | 10/2004 | Farrell et al. |
| 6,816,880 B1 | 11/2004 | Strandberg et al. |
| 6,842,906 B1 | 1/2005 | Bowman Amuah |
| 6,862,573 B2 | 3/2005 | Kendall et al. |
| 6,884,228 B2 | 4/2005 | Brown et al. |
| 6,934,848 B1 | 8/2005 | King et al. |
| 6,944,596 B1 | 9/2005 | Gray et al. |
| 6,949,079 B1 | 9/2005 | Westberg et al. |
| 6,976,164 B1 | 12/2005 | King et al. |
| 6,980,989 B2 | 12/2005 | Silverman et al. |
| 6,994,790 B2 | 2/2006 | Corbin et al. |
| 6,996,542 B1 | 2/2006 | Landry |
| 7,072,769 B2 | 7/2006 | Fletcher Haynes et al. |
| 7,076,032 B1 | 7/2006 | Pirasteh et al. |
| 7,087,047 B2 | 8/2006 | Kraus et al. |
| 7,169,352 B1 | 1/2007 | Felt et al. |
| 7,219,094 B2 | 5/2007 | Schiel et al. |
| 7,269,844 B2 | 9/2007 | Elteto et al. |
| 7,289,964 B1 | 10/2007 | Bowman-Amuah |
| 7,334,015 B1 | 2/2008 | Phillips |
| 7,354,415 B2 | 4/2008 | Bainbridge et al. |
| 7,373,373 B2 | 5/2008 | McElhannon |
| 7,380,024 B2 | 5/2008 | Peterson et al. |
| 7,415,438 B1 | 8/2008 | Berman et al. |
| 7,421,427 B2 | 9/2008 | DeForeest et al. |
| 7,430,478 B2 * | 9/2008 | Fletcher-Haynes et al. ... 702/21 |
| 7,434,166 B2 | 10/2008 | Acharya et al. |
| 7,454,399 B2 | 11/2008 | Matichuk |
| 7,475,143 B2 | 1/2009 | Hartmann et al. |
| 7,479,123 B2 | 1/2009 | Briggs |
| 7,540,021 B2 | 5/2009 | Page |
| 7,558,777 B1 | 7/2009 | Santos |
| 7,566,315 B2 | 7/2009 | Hirabuki |
| 7,574,376 B1 | 8/2009 | Berman et al. |
| 7,597,250 B2 | 10/2009 | Finn |
| 7,704,454 B1 | 4/2010 | Langley et al. |
| 7,708,710 B2 | 5/2010 | Min et al. |
| 7,739,227 B2 | 6/2010 | Jordan et al. |
| 7,752,178 B2 | 7/2010 | Anderson |
| 7,754,149 B2 * | 7/2010 | Sugiyama ...................... 422/67 |
| 7,844,472 B1 | 11/2010 | Akin et al. |
| 7,844,521 B1 | 11/2010 | Hoag et al. |
| 7,850,634 B2 | 12/2010 | Briggs |
| 7,860,726 B2 | 12/2010 | Connely et al. |
| 7,877,402 B1 | 1/2011 | Weiss et al. |
| 7,900,298 B1 | 3/2011 | Char et al. |
| 7,937,583 B2 | 5/2011 | Thornton et al. |
| 7,949,546 B1 | 5/2011 | Klieman et al. |
| 7,962,899 B2 | 6/2011 | McCullough et al. |
| 7,992,203 B2 | 8/2011 | Relyea |
| 8,036,987 B1 | 10/2011 | Grbac et al. |
| 8,060,382 B1 | 11/2011 | Lee et al. |
| 8,060,423 B1 | 11/2011 | Rukonic et al. |

(56) References Cited

U.S. PATENT DOCUMENTS

| | | |
|---|---|---|
| 8,060,500 B1 | 11/2011 | Fitch et al. |
| 8,086,730 B2 | 12/2011 | Ribak et al. |
| 8,108,227 B1 | 1/2012 | Rogers et al. |
| 8,108,271 B1 | 1/2012 | Duncan et al. |
| 8,146,000 B1 | 3/2012 | Boliek et al. |
| 8,155,950 B1 | 4/2012 | Bickerstaff |
| 8,166,473 B2 | 4/2012 | Kinsey et al. |
| 8,170,958 B1 | 5/2012 | Gremett et al. |
| 8,185,426 B1 | 5/2012 | Khoubyari |
| 8,196,061 B1 | 6/2012 | Bhojan |
| 8,204,805 B2 | 6/2012 | Eftekhari et al. |
| 8,209,229 B1 | 6/2012 | Weiss et al. |
| 8,214,276 B1 | 7/2012 | Preece et al. |
| 8,219,504 B1 | 7/2012 | Weiss et al. |
| 8,280,787 B1 | 10/2012 | Gandhi |
| 8,285,622 B1 | 10/2012 | Rao et al. |
| 8,286,199 B1 | 10/2012 | Pulaski et al. |
| 8,291,047 B2 | 10/2012 | Liu et al. |
| 8,296,206 B1 | 10/2012 | Del Favero et al. |
| 8,306,255 B1 | 11/2012 | Degnan |
| 8,321,309 B1 | 11/2012 | Jain et al. |
| 8,326,725 B2 | 12/2012 | Elwell et al. |
| 8,335,728 B1 | 12/2012 | Dahodwala et al. |
| 8,346,753 B2 | 1/2013 | Hayes |
| 8,346,929 B1 | 1/2013 | Lai |
| 8,352,350 B1 | 1/2013 | Del Favero et al. |
| 8,364,522 B1 | 1/2013 | Gevelber |
| 8,375,324 B1 | 2/2013 | Zubizarreta et al. |
| 8,380,590 B1 | 2/2013 | Rukonic et al. |
| 8,407,113 B1 | 3/2013 | Eftekhari et al. |
| 8,452,748 B1 | 5/2013 | Pugh |
| 8,463,622 B2 | 6/2013 | Garms et al. |
| 8,468,130 B2 | 6/2013 | Bhandari et al. |
| 8,473,263 B2 | 6/2013 | Tolone et al. |
| 8,473,858 B2 | 6/2013 | Buchanan et al. |
| 8,484,626 B2 | 7/2013 | Nagulu et al. |
| 8,495,596 B1 | 7/2013 | Safavi-Naini |
| 8,521,628 B1 | 8/2013 | Gowen et al. |
| 8,527,291 B1 | 9/2013 | Kochendorfer |
| 8,543,932 B2 | 9/2013 | Fields et al. |
| 8,566,313 B1 | 10/2013 | Zubizarreta et al. |
| 8,568,356 B2 | 10/2013 | Lebel et al. |
| 8,571,885 B2 | 10/2013 | Andros et al. |
| 8,600,835 B1 | 12/2013 | Lueck |
| 8,640,105 B2 | 1/2014 | Yaffe |
| 8,655,726 B1 | 2/2014 | Favero et al. |
| 8,660,945 B1 | 2/2014 | Pariante et al. |
| 8,688,504 B2 | 4/2014 | Reisman |
| 8,689,016 B2 | 4/2014 | Morten et al. |
| 8,707,409 B2 | 4/2014 | Shah et al. |
| 8,713,005 B2 | 4/2014 | Benson |
| 8,744,197 B2 | 6/2014 | Fertik et al. |
| 8,744,923 B1 | 6/2014 | McKay et al. |
| 8,751,292 B2 | 6/2014 | Del Favero et al. |
| 8,752,170 B1 | 6/2014 | Newstadt et al. |
| 8,768,833 B2 | 7/2014 | Freishtat et al. |
| 8,775,070 B1 | 7/2014 | Bhatia |
| 8,793,777 B2 | 7/2014 | Colson |
| 8,826,145 B1 | 9/2014 | Kirkpatrick et al. |
| 2002/0013523 A1 | 1/2002 | Csore et al. |
| 2002/0116219 A1 | 8/2002 | Ibok et al. |
| 2003/0004751 A1 | 1/2003 | Ng et al. |
| 2003/0032868 A1 | 2/2003 | Graskov et al. |
| 2003/0037023 A1 | 2/2003 | Lyakovetsky et al. |
| 2003/0040835 A1* | 2/2003 | Ng .................... A61B 5/14 700/214 |
| 2003/0069480 A1* | 4/2003 | Ng et al. ............... 600/300 |
| 2003/0120593 A1 | 6/2003 | Bansal et al. |
| 2003/0154108 A1 | 8/2003 | Fletcher-Haynes et al. |
| 2003/0200226 A1 | 10/2003 | Wells et al. |
| 2003/0229846 A1 | 12/2003 | Sethi et al. |
| 2004/0046787 A1 | 3/2004 | Henry et al. |
| 2004/0103040 A1 | 5/2004 | Ronaghi et al. |
| 2004/0117376 A1 | 6/2004 | Lavin et al. |
| 2004/0153432 A1 | 8/2004 | O'Halloran et al. |
| 2004/0193613 A1 | 9/2004 | Armand |
| 2004/0214148 A1* | 10/2004 | Salvino ................. A61N 1/39 434/262 |
| 2004/0267562 A1* | 12/2004 | Fuhrer et al. .............. 705/2 |
| 2005/0038675 A1 | 2/2005 | Siekman et al. |
| 2005/0071193 A1 | 3/2005 | Kalies |
| 2005/0096973 A1 | 5/2005 | Heyse et al. |
| 2005/0137908 A1 | 6/2005 | Fusari et al. |
| 2005/0182726 A1 | 8/2005 | Honeycutt et al. |
| 2005/0204900 A1 | 9/2005 | Burton |
| 2005/0234964 A1 | 10/2005 | Batra et al. |
| 2005/0240437 A1 | 10/2005 | Cunningham |
| 2005/0243655 A1 | 11/2005 | McCutcheon et al. |
| 2005/0278261 A1 | 12/2005 | Omanson et al. |
| 2006/0026067 A1 | 2/2006 | Nicholas et al. |
| 2006/0026519 A1 | 2/2006 | Vaindiner et al. |
| 2006/0075224 A1 | 4/2006 | Tao |
| 2006/0085478 A1 | 4/2006 | Landau et al. |
| 2006/0111943 A1 | 5/2006 | Wu |
| 2006/0190566 A1 | 8/2006 | Roach |
| 2006/0247971 A1 | 11/2006 | Dresden et al. |
| 2007/0055483 A1 | 3/2007 | Lee et al. |
| 2007/0106647 A1 | 5/2007 | Schwalb |
| 2007/0112574 A1 | 5/2007 | Greene |
| 2007/0130111 A1 | 6/2007 | Stoudt et al. |
| 2007/0143660 A1 | 6/2007 | Huey et al. |
| 2007/0198744 A1 | 8/2007 | Wensley et al. |
| 2007/0219826 A1 | 9/2007 | Brodsky et al. |
| 2007/0220494 A1 | 9/2007 | Spooner |
| 2007/0250390 A1 | 10/2007 | Lee et al. |
| 2007/0276678 A1 | 11/2007 | Nichols |
| 2008/0097952 A1 | 4/2008 | Eswaran |
| 2008/0132311 A1 | 6/2008 | Walker |
| 2008/0133551 A1 | 6/2008 | Wensley et al. |
| 2008/0133736 A1 | 6/2008 | Wensley et al. |
| 2008/0148160 A1 | 6/2008 | Holmes et al. |
| 2008/0203523 A1 | 8/2008 | Anderson et al. |
| 2008/0208750 A1 | 8/2008 | Chen |
| 2009/0037264 A1 | 2/2009 | Del Favero et al. |
| 2009/0037266 A1 | 2/2009 | Weiss et al. |
| 2009/0048870 A1 | 2/2009 | Godshall et al. |
| 2009/0076885 A1 | 3/2009 | Fein et al. |
| 2009/0187462 A1 | 7/2009 | Gevelber et al. |
| 2009/0191174 A1 | 7/2009 | Boudreau et al. |
| 2009/0204964 A1 | 8/2009 | Foley et al. |
| 2009/0288037 A1 | 11/2009 | Lawton et al. |
| 2010/0049542 A1 | 2/2010 | Benjamin et al. |
| 2010/0049576 A1 | 2/2010 | Wilson et al. |
| 2010/0063838 A1 | 3/2010 | Schumacher et al. |
| 2010/0083358 A1 | 4/2010 | Govindarajan et al. |
| 2010/0100424 A1 | 4/2010 | Buchanan et al. |
| 2010/0138241 A1 | 6/2010 | Ruark et al. |
| 2010/0142447 A1 | 6/2010 | Schlicht et al. |
| 2010/0205112 A1 | 8/2010 | Reynolds et al. |
| 2010/0215280 A1 | 8/2010 | Abdo et al. |
| 2010/0256974 A1 | 10/2010 | Xu et al. |
| 2010/0269049 A1 | 10/2010 | Fearon |
| 2010/0306080 A1 | 12/2010 | Trandal et al. |
| 2011/0010214 A1 | 1/2011 | Carruth |
| 2011/0022425 A1 | 1/2011 | Block et al. |
| 2011/0041153 A1 | 2/2011 | Simon et al. |
| 2011/0047230 A1 | 2/2011 | McGee |
| 2011/0106759 A1 | 5/2011 | Brown |
| 2011/0130114 A1 | 6/2011 | Boudville |
| 2011/0191254 A1 | 8/2011 | Womack |
| 2012/0010553 A1 | 1/2012 | Alqvist et al. |
| 2012/0016721 A1 | 1/2012 | Weinman |
| 2012/0022892 A1 | 1/2012 | Feldman et al. |
| 2012/0036565 A1 | 2/2012 | Gamez et al. |
| 2012/0054625 A1 | 3/2012 | Pugh et al. |
| 2012/0072232 A1 | 3/2012 | Frankham et al. |
| 2012/0096021 A1 | 4/2012 | Wiser et al. |
| 2012/0130962 A1 | 5/2012 | Wiser et al. |
| 2012/0136678 A1 | 5/2012 | Steinberg |
| 2012/0173397 A1 | 7/2012 | Elwell et al. |
| 2012/0191703 A1 | 7/2012 | Huff |
| 2012/0191716 A1 | 7/2012 | Omoigui |
| 2012/0215560 A1 | 8/2012 | Ofek et al. |
| 2012/0253801 A1 | 10/2012 | Santos-Lang et al. |

(56) References Cited

U.S. PATENT DOCUMENTS

| | | |
|---|---|---|
| 2012/0329529 A1 | 12/2012 | van der Raadt |
| 2013/0030889 A1 | 1/2013 | Davich et al. |
| 2013/0061323 A1 | 3/2013 | Liske |
| 2013/0138501 A1 | 5/2013 | Litzow et al. |
| 2013/0204778 A1 | 8/2013 | Connors et al. |
| 2013/0290408 A1 | 10/2013 | Stephure et al. |
| 2013/0291024 A1 | 10/2013 | Lefevre et al. |
| 2013/0297349 A1 | 11/2013 | Epstein et al. |
| 2013/0304496 A1 | 11/2013 | Rangadass |
| 2013/0346144 A1 | 12/2013 | Ferren et al. |
| 2013/0346527 A1 | 12/2013 | Shah et al. |
| 2014/0033230 A1 | 1/2014 | Hanna et al. |
| 2014/0088998 A1 | 3/2014 | Boyer et al. |
| 2014/0156345 A1 | 6/2014 | Eskey et al. |
| 2014/0164484 A1 | 6/2014 | Vonog et al. |
| 2014/0172625 A1 | 6/2014 | Reisman |

FOREIGN PATENT DOCUMENTS

| | | |
|---|---|---|
| CN | 1674030 A | 9/2005 |
| CN | 101982006 A | 2/2011 |
| JP | 08-240589 A | 9/1996 |
| KR | 2003-0063426 | 7/2003 |
| KR | 2005-0072937 | 7/2005 |
| KR | 2005-0075502 A | 7/2005 |
| KR | 2008-0017470 A | 2/2008 |
| WO | WO02/069793 A2 | 9/2002 |

OTHER PUBLICATIONS

Bancroft et al.; U.S. Appl. No. 14/727,745 entitled "Systems and methods for managing blood donations," filed Jun. 1, 2015.

World Health Organization; WHO guidelines on drawing blood; ©2010; 127 pgs.; retrieved from the internet (http://www.who.int/injection_safety/phleb_final_screen_ready.pdf) printed on or before Jun. 8, 2016.

World Health Organization; WHO guidelines on drawing blood; ©2010; 5 pages; retrieved from the internet (http://www.ncbi.nlm.nih.gov/books/NBK138671) on Aug. 14, 2015.

* cited by examiner

| Network Status | Recent Draws | | System Utility | Release Data | Options | | Hide Display | |
|---|---|---|---|---|---|---|---|---|

| ID | Stat | Flow | ml | Target | Time | Error | Donation ID | Batt | Calibration | Radio |
|---|---|---|---|---|---|---|---|---|---|---|
| Scale 10 | Mid-Draw | 6 | 325 | 470 | 06:25 | - - - | G1234983546 | 66% | 28-Feb, 08:34 | 70% |
| Scale 24 | Inactive | 0 | 0 | 470 | 0:00 | - - - | | 100% | 28-Feb, 08:35 | 65% |
| Scale 52 | End-Recovery | 0 | 474 | 470 | 08:45 | Low Flow | G1234996745 | 66% | 28-Feb, 08:36 | 75% |
| Scale 07 | Inactive | 0 | 0 | 470 | 0:00 | - - - | | 33% | 28-Feb, 08:37 | 65% |
| Scale 63 | Inactive | 0 | 0 | 470 | 0:00 | - - - | | 33% | 28-Feb, 08:39 | 65% |
| Scale 53 | Inactive | 0 | 0 | 470 | 0:00 | - - - | | 100% | 28-Feb, 08:42 | 65% |
| Scale 15 | Inactive | 0 | 0 | 470 | 0:00 | - - - | | 100% | 28-Feb, 08:45 | 65% |
| Scale 22 | Start-Scan | 0 | 0 | 470 | 0:00 | - - - | G12346678594 | 66% | 28-Feb, 08:50 | 65% |
| Scale 33 | Inactive | 0 | 0 | 470 | 0:00 | - - - | | 66% | 28-Feb, 08:51 | 65% |
| Scale 65 | Inactive | 0 | 0 | 470 | 0:00 | - - - | | 100% | 28-Feb, 08:52 | 65% |

FIG. 2A

| Network Status | Recent Draws | System Utility | Release Data | Options | Hide Display |

| ID | Stat | ml | Target | Time | Error | Donation ID | Batt | Calibration | Radio |
| --- | --- | --- | --- | --- | --- | --- | --- | --- | --- |
| Scale 65 | Complete | 470 | 470 | 08:00 | - - - | G1234983546 | 66% | 28-Feb, 08:34 | 70% |
| Scale 33 | Complete | 470 | 470 | 08:00 | - - - | G1234983477 | 100% | 28-Feb, 08:35 | 65% |
| Scale 07 | Timeout | 380 | 470 | 15:00 | Timeout | G1234996745 | 66% | 28-Feb, 08:36 | 75% |
| Scale 63 | Complete | 470 | 470 | 08:00 | - - - | G1234983542 | 33% | 28-Feb, 08:37 | 65% |
| Scale 10 | Complete | 470 | 470 | 08:00 | - - - | G1234983470 | 33% | 28-Feb, 08:39 | 65% |
| Scale 52 | Complete | 495 | 470 | 08:00 | - - - | G1234996788 | 100% | 28-Feb, 08:42 | 65% |
| Scale 33 | Complete | 470 | 470 | 08:00 | - - - | G1234983503 | 100% | 28-Feb, 08:45 | 65% |
| Scale 10 | Complete | 470 | 470 | 08:00 | - - - | G1234983447 | 66% | 28-Feb, 08:50 | 65% |
| Scale 07 | Complete | 470 | 470 | 08:00 | - - - | G1234996711 | 66% | 28-Feb, 08:51 | 65% |
| Scale 15 | Complete | 470 | 470 | 08:00 | - - - | G1234996780 | 100% | 28-Feb, 08:52 | 65% |

Staff ID Barcode No. 1

| | Type | | | Exact String | Field Size |
|---|---|---|---|---|---|
| Field 1 | Exact String | ▽ | | =G1234 | 6 ▽ |
| Field 2 | Numeric/Match ID | ▽ | | | 5 ▽ |
| Field 3 | Alpha/Match ID | ▽ | | | 3 ▽ |
| Field 4 | Numeric/No Match | ▽ | | | 2 ▽ |
| Field 5 | {not used} | ▽ | | | 0 ▽ |
| Field 6 | {not used} | ▽ | | | 0 ▽ |
| Field 7 | {not used} | ▽ | | | 0 ▽ |
| Field 7 | {not used} | ▽ | | | 0 ▽ |

Example =G12345555ABC99    Total Length= 16

When Start of Donation ▽    Sequence Order No. 2 ▽

Display Nurse ID
20 Char Max

Network Status | Recent Draws | System Utility | Release Data | Options | Hide Display

FIG. 4

| Network Status | Recent Draws | System Utility | Release Data | Options | Hide Display |

*Barcode Summary Table*

| Seq Order | Name | Display Name | Example | Length | Match ID | When |
|---|---|---|---|---|---|---|
| 1 | Donation ID | Main Bag ID | =ABCD12345098756 | 16 | No | Start |
| 2 | Donor ID | Donor Card | =%55559999 | 12 | No | Start |
| 3 | Technician ID-1 | Nurse at Start | =&1234555555ABC00 | 16 | Yes | Start |
| 4 | Product Code | Product Code | =(45674 | 7 | No | Start |
| 5 | Sample Tube 1 | Tube 1 | =ABCD12345098756 | 16 | Yes | Flex |
| 6 | Sample Tube 2 | Tube 2 | =ABCD12345098756 | 16 | Yes | Flex |
| 7 | Technician ID-2 | Nurse at End | =&1234555555ABC00 | 16 | Yes | End |

FIG. 5

SYSTEMS AND METHODS FOR MANAGING BLOOD DONATIONS

CROSS REFERENCE TO RELATED APPLICATIONS

This application claims the benefit under 35 U.S.C. 119 of U.S. Provisional Patent Application No. 61/474,679, filed Apr. 12, 2011, titled "SYSTEMS AND METHODS FOR MANAGING BLOOD DONATIONS". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

Described herein are devices and methods for use in blood donation and blood management. In particular, described herein are devices and methods for acquiring blood donations and managing information related to the blood donations.

SUMMARY OF THE DISCLOSURE

In one embodiment, a method of monitoring real time blood draw information is provided, comprising collecting blood from a patient with a blood collection device, while collecting blood from the patient, turning on a transmit function of the blood collection device to transmit blood collection data from the blood collection device to a control system, turning off the transmit function of the blood collection device after the blood collection data is received by the control system, and waiting for a time interval before again turning on the transmit function of the blood collection device.

In some embodiments, the time interval is up to 30 seconds in length.

In other embodiments, the blood collection data is selected from the group consisting of a donation ID, a staff ID, a volume of blood collected, a flow rate of blood collected, a status of the blood collection device, and errors during collection of blood.

In one embodiment, the collecting blood step further comprises collecting blood from a patient with a plurality of blood collection devices. In an additional embodiment, the method further comprises, at multiple times while collecting blood from the patient, turning on a transmit function of a plurality of blood collection devices to transmit blood collection data from the blood collection devices to a control system, turning off the transmit function of the plurality of blood collection devices after the blood collection data is received by the control system, and waiting for a time interval before again turning on the transmit function of the plurality of blood collection devices.

In some embodiments, the collecting step comprises automatically collecting blood from the patient with the blood collection device.

In other embodiments, the method further comprises turning on the transmit function of the blood collection device at least once after blood has been collected from the patient.

A method of updating firmware on a plurality of blood collection devices is provided, comprising selecting a first blood collection device as a master device and designating one or more additional blood collection devices as slave devices, wherein each blood collection device is configured to collect and measure blood collection, sending a request for a firmware update to a control system from just the master device and not the slave devices, transmitting the firmware update from the control system to the master and slave devices, wherein the master device communicates with the control system while the slave devices passively listen, and replacing a base firmware on the master and slave devices with an upgraded firmware from the control system.

In some embodiments, the blood collection devices are in wireless communication with the control system.

In other embodiments, the replacing step comprises simultaneously replacing the base firmware on the blood collection devices with the upgraded firmware from the control system.

In one embodiment, the replacing step further comprises replacing the base firmware on the master and slave devices with the upgraded firmware from the control system simultaneously.

Some embodiments further comprise employing measures to insure data integrity of data stored on the blood collection devices.

In another embodiment, the method further comprises employing measures to insure data integrity of a collection device configuration.

A method of specifying the collection protocol for a blood collection device is provided, the method comprising specifying in a blood collection control system, a first input, specifying in the blood collection control system, a first time during a blood collection event for the blood collection device to request the first input, specifying in the blood collection control system, a second input, specifying in the blood collection control system, a second time during the blood collection event for the blood collection device to request the second input, compiling in the blood collection control system a blood collection protocol including the first and second inputs and the first and second times, and transmitting the blood collection protocol from the blood collection control system to one or more blood collection devices.

In one embodiment, the first and second inputs are barcodes.

In another embodiment, the specifying input steps comprise specifying length and character type requirements for the barcodes.

In some embodiments, the first time is at the beginning of a blood collection process. In another embodiment, the second time is at the end of a blood collection process.

In one embodiment, the first input is a donation ID. In another embodiment, the second input is a staff ID.

In another embodiment, the first time is at the beginning of a blood collection process. In some embodiments, the second time is at the beginning of a blood collection process.

In one embodiment, the first input is a biometric input. The biometric input can be a fingerprint, for example.

In another embodiment, the first input is a product code.

A blood collection and monitoring system is provided, comprising a control system, a blood collection device in communication with the control system, the blood collection device being configured to collect blood from a patient and to collect blood collection data relating to the collected blood, the blood collection device further comprising a transmitter configured to periodically turn on a transmit function to transmit the blood collection data from the blood collection device to the control system.

In some embodiments, the transmitter of the blood collection device is configured to turn off once the blood collection data has been transmitted to the control system. In another embodiment, the transmitter of the blood collection device automatically turns on again after a preset time. In some embodiments, the preset time is less than 30 seconds in length.

A blood collection system is also provided, comprising a master blood collection device and a plurality of slave blood collection devices, each blood collection device being configured to collect and measure blood collection, a control system configured to receive a request for a firmware update from only the master blood collection device and not the slave blood collection devices, the control system further configured to transmit the firmware update to the master and slave blood collection devices, wherein the control system is configured to communicate with the master blood collection while the slave devices passively listen to replace a base firmware on the master and slave blood collection devices with an upgraded firmware from the control system.

In some embodiments, the control system comprises a wireless transceiver configured to receive the request from the master blood collection device and to transmit the firmware update to the master and slave blood collection devices.

DETAILED DESCRIPTION OF THE DISCLOSURE

Figure 1A:
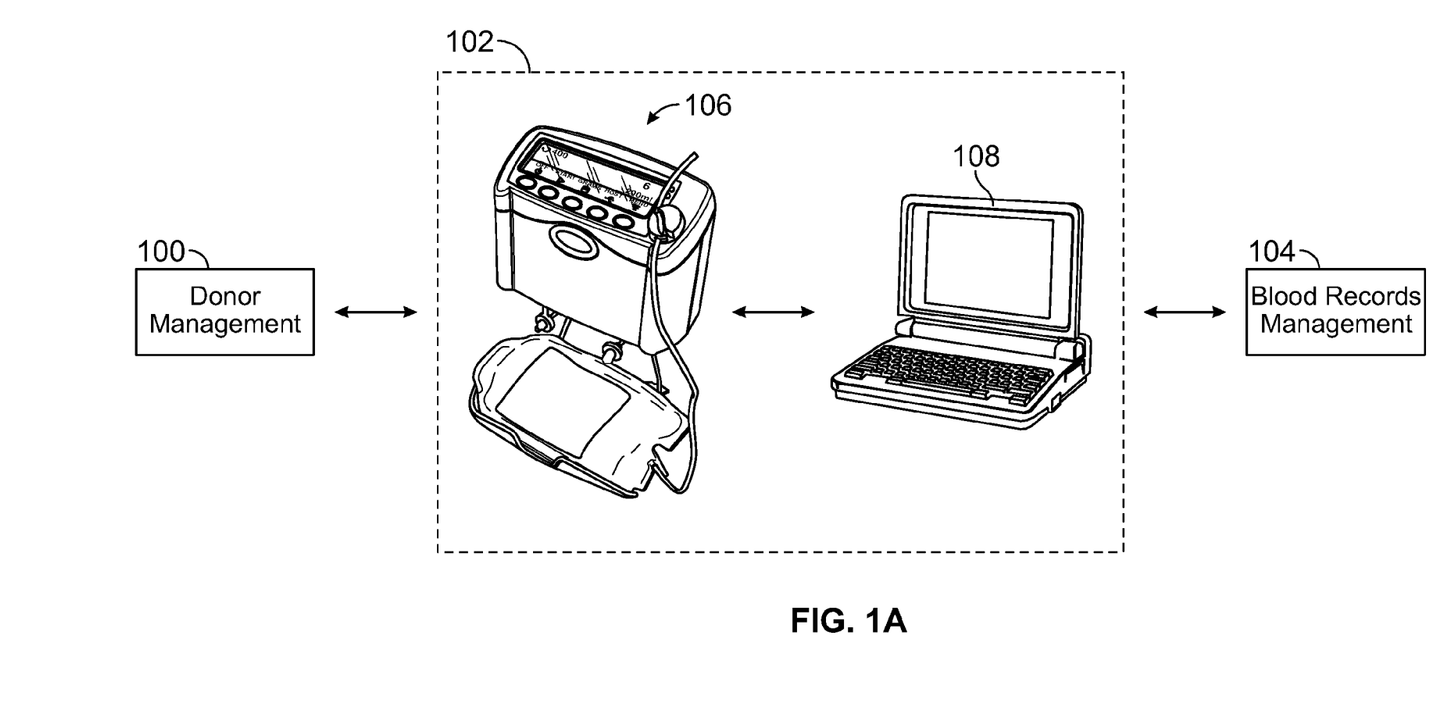
FIG. 1A is a schematic illustration of a blood donation process.

FIG. 1A is a schematic illustration of a blood donation process, starting with a donor registration and management process 100, followed by a blood and data collection process 102, and finally a blood records management process 104. Typically, the donor management process 100 comprises recruiting and locating willing blood donors, determining if blood donors are fit to donate blood, scheduling blood donations, and retaining blood donors for future donations.

The next step of the blood donation process, the blood and data collection process 102, can comprise the collection of a blood donation from a blood donor, as well as collection of information relating to the collection of the blood donation. In some embodiments, the blood and data collection process 102 can comprise a blood collection device 106 and a control system 108, which can be software code stored and executed on a computer system or network. The information relating to the collection of blood donations can comprise, for example, time and location of the blood collection, amount of blood withdrawn, blood type, employee ID of the phlebotomist responsible for collection of the blood, elapsed time of blood collection, interruptions of the blood donation process, etc.

Finally, once the blood donation is completed, the blood records management process 104 is responsible for managing and storing blood stockpiles, tracking stored volumes of the various blood types, and distributing the blood to places in need of blood donations (e.g., hospitals and other medical centers).

Figure 1B:
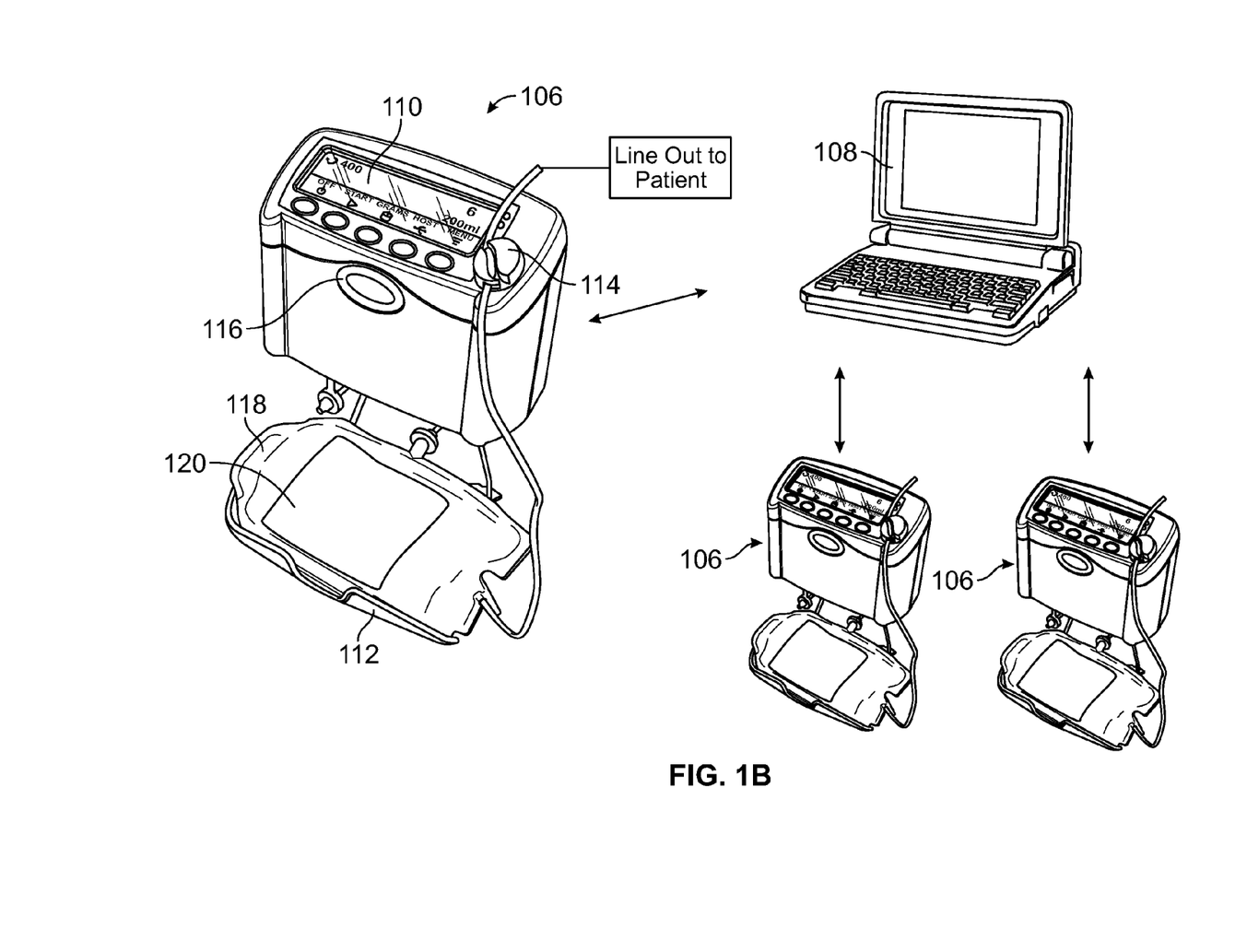
FIG. 1B is an illustration of a blood collection device and a control system.

FIG. 1B is a diagram showing the blood collection device 106 and control system 108 of FIG. 1A. As shown in FIG. 1B, in some embodiments, more than one blood collection device 106 can be networked with and bi-directionally communicate with the control system 108. Blood collection device 106 is configured to provide blood banks and other blood collection centers with an inexpensive yet accurate means of monitoring the collection of blood donations. The device is configured to accurately weigh blood donations during the collection process and to provide blood bag mixing insuring correct disbursement of anticoagulant and alleviating the need for manual mixing by a phlebotomist. Referring to FIG. 1B, blood collection device 106 can include a graphical user interface (GUI) 110, a scale or bag tray 112, a pinch valve 114, and a barcode scanner 116. The device can be configured to receive a blood donation bag 118 on the scale and pinch valve, as shown. In some embodiments, the blood donation bag comprises a barcode 120 readable via the barcode scanner of the blood collection device.

The GUI 110 allows a user (e.g., a phlebotomist) to configure, calibrate, and setup the blood collection device for use. In some embodiments, the GUI 110 displays information to the user such as calibration status of the device bag tray 112, weight of the blood donation bag 118, and operation status of the device (e.g., calibration, blood collection underway, blood collection complete, errors during collection, etc). During initial setup of the device, a user may be asked to zero or calibrate the device, with no weight on the bag tray 112 to ensure accurate measurement of collected blood.

In some embodiments, the device comprises an agitation system suspended on the internal load cell. The agitation system can comprise a motor-driven crank configured to agitate/shake the bag during blood collection. The agitation system has been designed for minimal weight and optimized for the power required to agitate/shake the bag tray 112 and thus, the blood bag.

When a blood collection bag is placed on the bag tray 112, vertical oscillations of the agitation system can cause blood collected from a donor to flow from one end of the bag to the other, resulting in gentle mixing of the blood and the contained anticoagulant. Since the agitation system can be mounted on the internal load cell, the load cell can then sense the weight of the bag tray 112, the agitation system, the blood bag, and the accumulated blood.

The blood collection device can further include a pinch valve 114 configured to open and close the blood bag line leading from the patient to the blood donation bag 118. Thus, the blood collection device can be configured to open the pinch valve 114 when the blood collection process begins and close the pinch valve when the blood collection is complete.

The blood collection device can be configured to automatically measure the weight of accumulated blood during the blood collection process. In some embodiments, the weight of the accumulated blood is measured every time the blood bag and bag tray 112 are in a relatively stable position. In other embodiments, the accumulated blood is measured continuously. By regularly monitoring the weight of collected blood, the blood collection device can calculate blood flow rates from the patient to the blood collection bag. The weight measurements and or flow rates can be used to determine when the blood collection process is complete.

When a blood collection is started, the blood collection device can first implement a series of weight readings of the empty blood bag, the agitation system, and the bag tray assembly. This can be recorded in the device's memory as the tare weight. The desired collection volume can be converted mathematically from weight to volume by using the constant specific gravity of blood of 1.058. (1.00 ml of blood weighs 1.058 grams). This converted weight value plus the tare weight results in the target weight and is compared against on-going weight readings as the collection proceeds. The blood collection device can then open the pinch valve to begin the blood collection process.

The agitation system can be left off until a small increase in weight is seen over the tare weight. As soon as the weight increase is seen by the blood collection device, the agitation system can initiate the shacking/rocking, and various other timing and flow functions can be activated. The blood collection device can continue to read the weight of the blood collection bag. Although these readings are relatively accurate, in some embodiments for greater accuracy, the blood collection system can stop the agitation process when the total weight is slightly less than the target weight. The final readings of collected blood can then be taken with the bag and bag tray in a horizontal position. At this point, it is unnecessary to continue agitating the bag since the anticoagulant is already fully mixed with the blood in the bag. Alternatively, the shaking/rocking could continue throughout the collection provided that accuracy of the weight readings could be assured.

Since blood bank standards require that blood collections must be completed in a set period of time (20 minutes maximum for current US regulations), smaller volumes of collection can tolerate a slower flow rate. In some embodiments, the blood collection device measures the flow rate and compares it against a computed constant, equal to a minimum flow value for the set period of time described above. As a result, if the required volume is greater, the flow rate must be greater to accomplish the fill in the set period of time (e.g., 20 minutes). If the required volume is less, the flow rate can be slower.

The blood collection device 106 can also include a barcode scanner 116 configured to read a barcode as an input to the device. For example, donation ID's unique to individual donor can be scanned during the blood collection process to keep track of all collection events related to that unique donation ID. In FIG. 2B, the donation ID can be represented as a barcode 120 located on blood donation bag 118.

The blood collection device 106 can be in communication with control system 108 during all steps of the blood collection process described above (e.g., calibration, blood collection, and completion of the blood draw). The blood collection device and control system can communicate via any technology known in the art, such as wirelessly through a WiFi or Bluetooth connection, or through a wired Ethernet connection. The control system can comprise a computer having all the necessary hardware (e.g., CPU, memory, data storage, etc) required to execute a data collection and management software.

The data collection and management software of control system 108 will now be described. The software creates the interface between one or more blood collection devices and a facility's blood data management system.

In some embodiments, the software allows viewing and printing of blood collection device(s) data as well as remote configuration and setup of the blood collection devices. In some embodiments, the data collection and management software of the control system 108 can be used to setup the blood collection devices 106 with which it is in communication. The control system can be used to specify which parameters are used during a blood draw by each of the blood collection devices. For example, a standard blood draw may require that 500 ml of blood be taken from a patient, and thus all blood collection devices can be preconfigured to automatically draw 500 ml of blood from each patient. If, however, a patient is cleared to give only 450 ml of blood, then the control system can be used to change the blood draw volume on a particular blood collection device from 500 ml to 450 ml. To accomplish this, the new blood volume of 450 ml can be entered into the control system 108, then the blood collection device that will be used for that particular patient can "pull" the updated configuration from the control system (e.g., by syncing the blood collection device with the control system).

The software of control system 108 can also be configured to remotely update the firmware of all blood collection devices in communication with the control system. One method of updating the firmware on a plurality of blood collection devices can be described referring to FIG. 1B. A single blood collection device can be set as a "Master" device, and the remaining blood collection devices can be set as "Slave" devices. The "Master" device can then request a firmware upgrade from the control system 108 and then "listen" for a response from the control system, specific to that device. While the "Master" device is requesting the firmware upgrade, the "Slave" devices enter a "listen" mode as well, where they wait for any new firmware instructions from the control system. When the control system receives the firmware upgrade request from the "Master" device, the control system can then transmit the firmware upgrade, if available, to all listening devices, including both the "Master" and "Slave" devices. All devices can then upgrade to the new firmware simultaneously, at the same time, instead of each having to individually request and receive a firmware upgrade from the control system.

The data collection and management software can employ measures to insure data integrity and prevent unauthorized actions by the user to either the data or the blood collection device configuration. These measures can include individual record checksums, as well as username and password protection to configuration utilities and data file transfer, renaming or deletion ("release"). The software system can also protect against data loss by retention of up to 150 or more donation records within each blood collection device, for retransmission to the software.

Figure 2A:
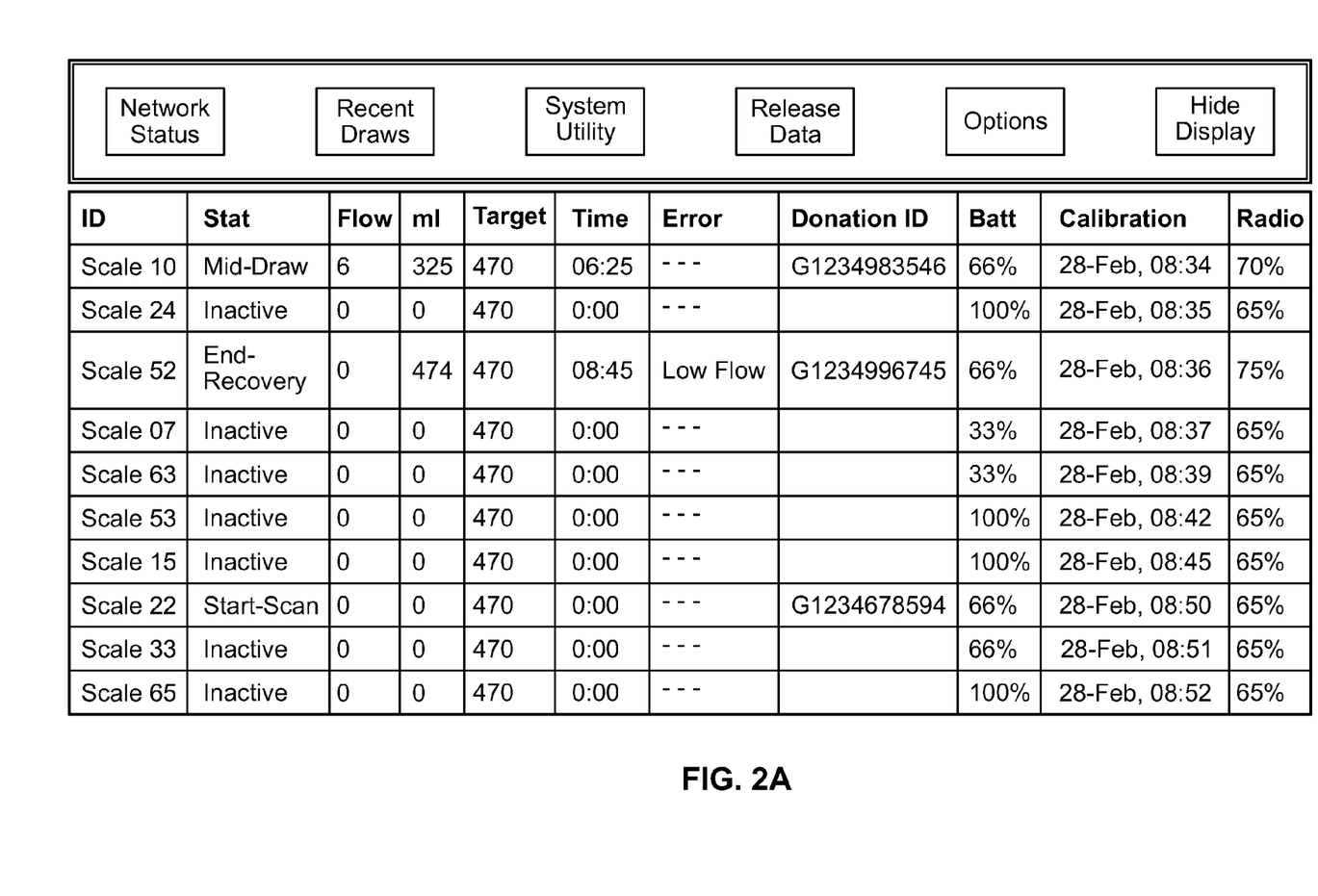
FIGS. 2-5 illustrate various features of a blood data management system.
Figure 2B:
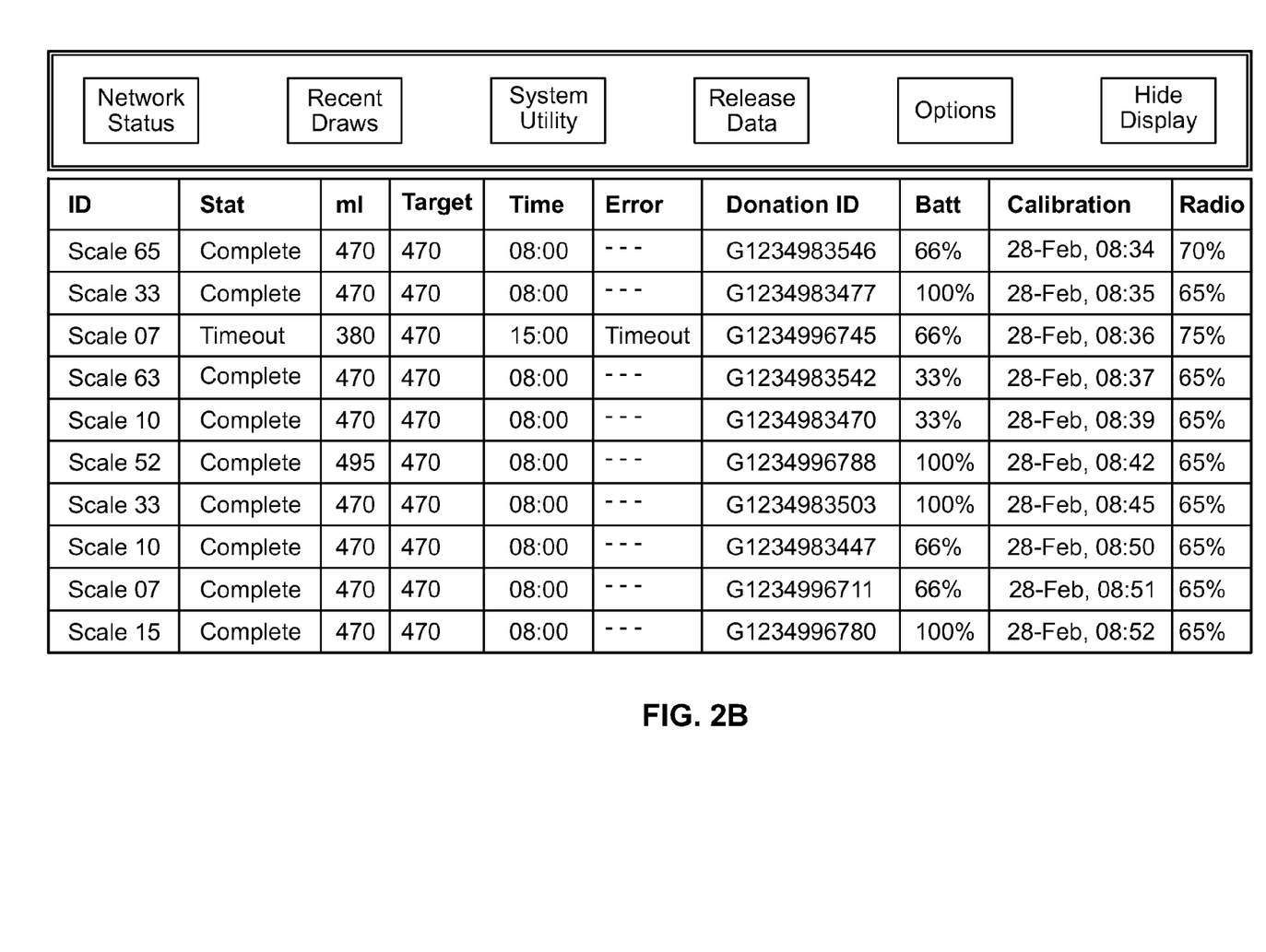

FIGS. 2A-2B illustrate one embodiment of a graphical interface for the data collection and management software. In FIG. 2A, the "Network Status" tab can display the status of all inactive and currently active blood collection devices communicating with the control system. For example, referring to FIG. 2A, each row represents a separate blood collection device (such as blood collection devices 106 in FIG. 1B), represented by a unique device ID, shown in the "ID" column. The "Stat" column displays the status of each device. When a device is not in use, the status can read "Inactive." When the device is in the middle of a blood collection process, the status can read "Mid-Draw." The beginning of a blood collection process can be displayed as a status of "Start-Scan," and the end of a blood collection process can be displayed as a status of "End-Recovery."

The "Network Status" tab can also display other parameters relevant to the devices being monitored and the blood collection process. For example, the Flow Rates of blood being collected by each device ("Flow" column), the total amount of blood drawn ("ml" column), the target volume of blood to draw ("Target" column), the duration of the blood draw ("Time" column), whether there is an error in the blood draw ("Error" column), the donation ID of the patient ("Donation ID" column), as well as battery, calibration, and wireless communication values of each device ("Batt", "Calibration", and "Radio" columns, respectively) can all be displayed in real time or quasi real time by the software. Other parameters can be monitored and tracked by the software that are not shown in FIG. 2A. For example, the staff ID of the person performing the blood draw can be monitored and recorded. Additionally, secondary donation ID's, Sample Tube ID's, serial numbers of the blood collection devices, and the location and time of the blood draw can be tracked and/or scanned.

As mentioned above, the "Network Status" tab provides information regarding errors that occur during a blood collection process. In some situations, the error can be related to a malfunction in the blood collection device itself. By tracking the error rates of specific devices, the control system software can be configured to track and identify specific blood collection devices with higher failure/error rates than normal. Similarly, the control system software can be configured to track if a particular staff member (e.g., nurse, phlebotomist) is the supervising staff member on a higher number of blood draw cases that result in errors. This can be used as a tool to identify problems with a particular staff member's performance.

In some embodiments, the information is displayed in real time, and each blood collection device continuously updates the software of the control system with the current values of data or status of each device being monitored. However, in other embodiments, the blood collection device can update these parameters in quasi real time, that is, the device can update the parameters to the software periodically after a preset period of time (e.g., every 30 seconds, every minute, every 5 minutes, etc).

In one embodiment of a quasi real time configuration, the blood collection device can be configured to automatically "turn on" a transmit signal after the preset period of time to transmit the collected parameters to the control system software. Upon completion of the data transmission, the blood collection device can then be configured to automatically "turn off" the transmit signal after the blood collection data is received by the control system. Although the blood collection device continues to collect data relating to the blood draw when the transmit signal is off, transmitting or uploading the data to the control system only periodically, saves power and can allow a blood collection device to operate on battery power for weeks at a time instead of only days. In some embodiments, the blood collection device can be configured to wait a time interval (e.g., the preset time above) before again turning on the transmit function of the blood collection device. The collected parameters that can be transmitted can include, among others, a donation ID, a staff ID, a volume of blood collected, a flow rate of blood collected, a status of the blood collection device, or errors during collection of blood.

FIG. 2B illustrates a "Recent Draws" tab in the software that can display all of the information described above (e.g., device ID, Status, amount of blood drawn, target volume of blood, duration of blood draw, error messages, donation ID, battery, calibration, and radio values) for blood collection events that have occurred in the past. In some embodiments, the "Recent Draws" tab displays this information for past blood collection events that have not yet been uploaded or "released" from the software system to another computer system or network device. The "Release Data" tab can release all of the past blood collection events and data from the "Recent Draws" tab to a location specified by the user. For example, the data can be released as a data file onto the local computer system, or alternatively, can be uploaded and released to a remote system.

Figure 3:
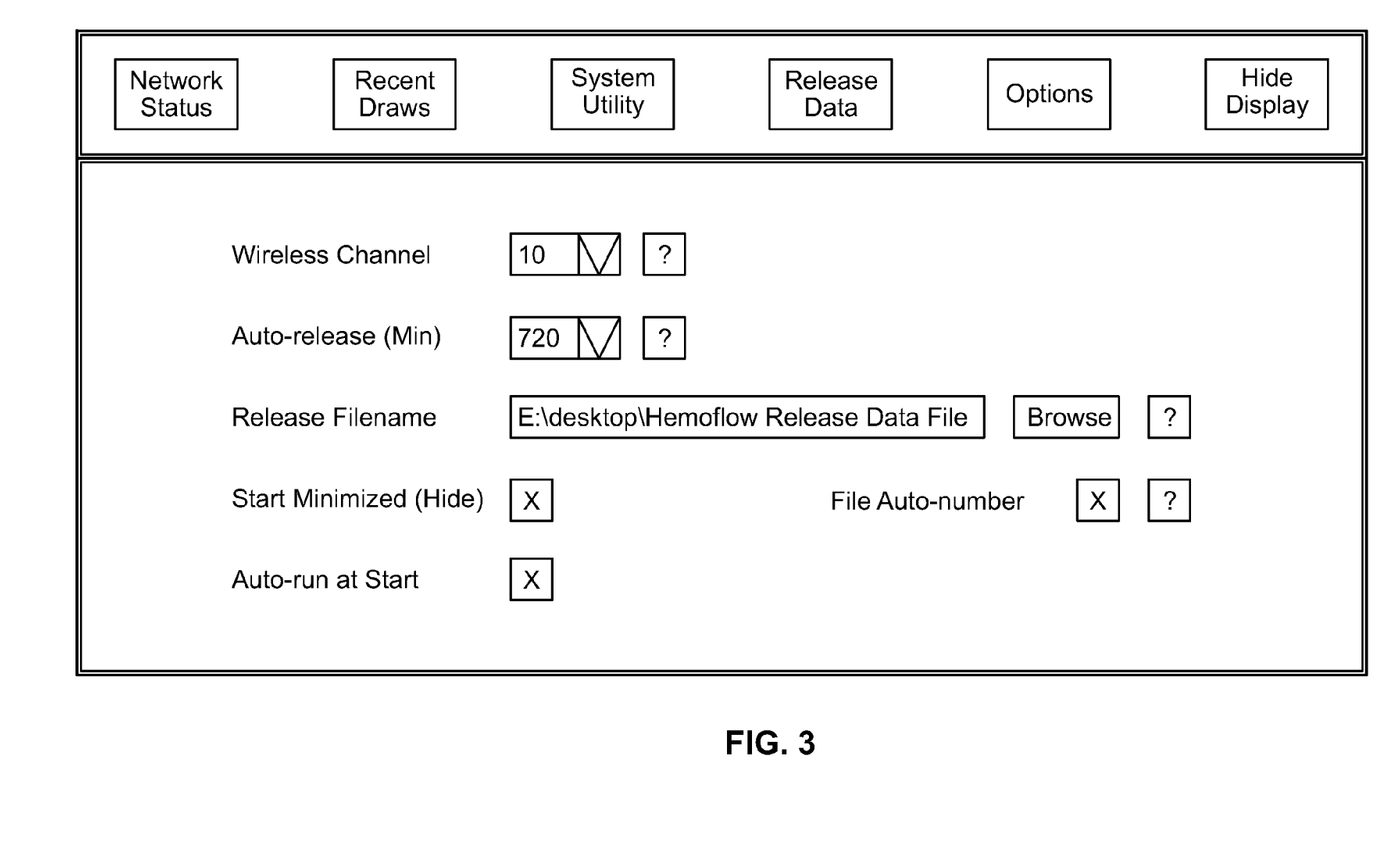

The "Options" tab in the software can allow individual configuration of several options within the software. For example, referring to FIG. 3, a user can configure how and when to release the "Recent Draws" data. As shown in FIG. 3, the data can be configured to be automatically released after a set period of time (e.g., every 720 minutes in FIG. 3), and the location and name of the data file to be created can be specified (e.g., "Hemoflow Release Data File" to be stored on the computer "desktop").

The "Options" tab also allows vast customization of various inputs into the blood collection device. For example, in many embodiments, the blood collection device can be configured to scan a unique identifier as an input (e.g., scan a barcode with barcode scanner incorporated in the blood collection device, or scan a biological feature, such as a fingerprint, with a biometric scanner incorporated in the blood collection device). When a barcode is used as an input into the blood collection device, various features of the barcode itself can be customized in the software.

Figure 4:
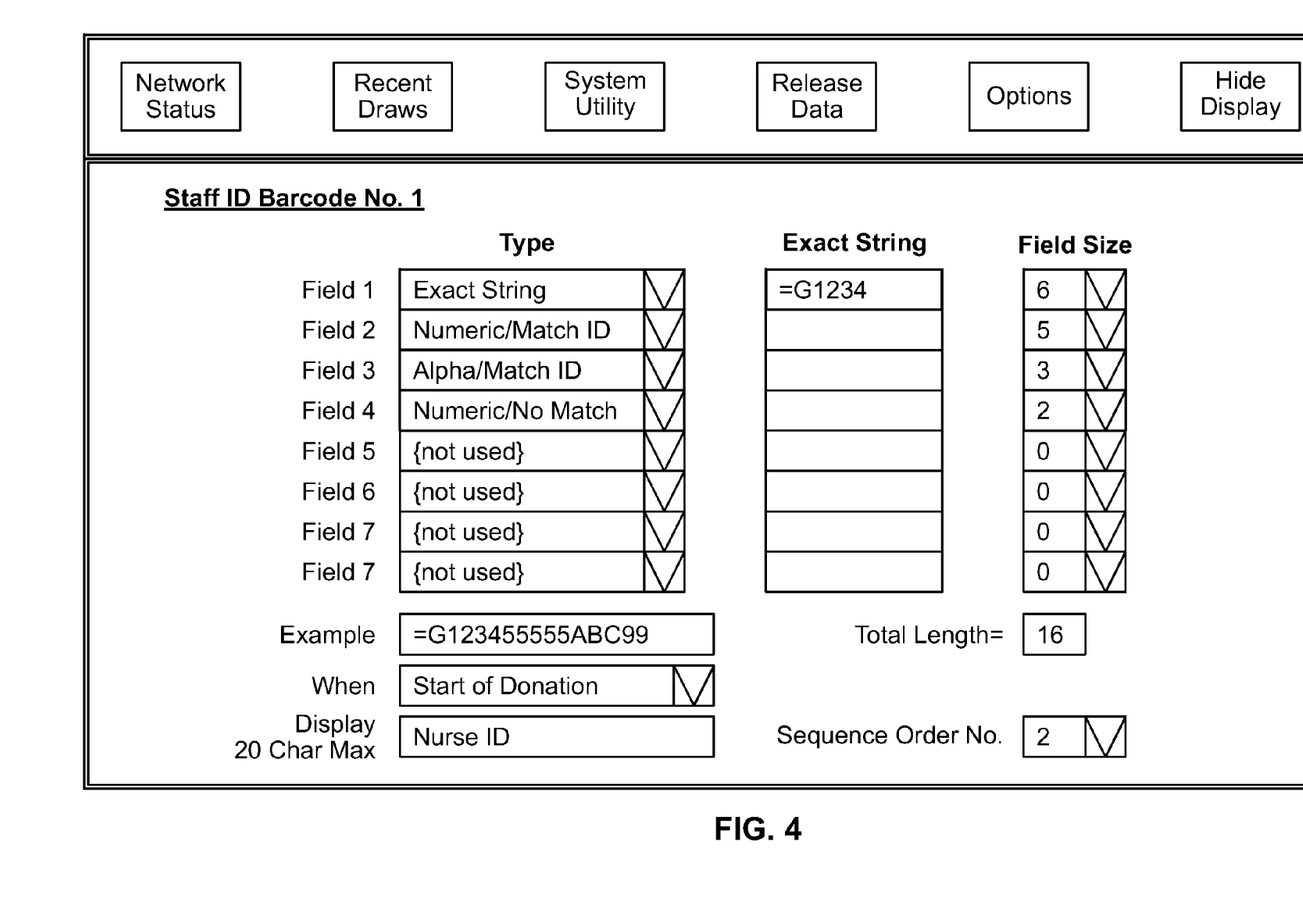

FIG. 4 illustrates how to customize various barcode components in the software to be used within a blood collection process. The length of a barcode, the type of barcode, and the order in which each particular barcode is to be scanned during a blood collection process can be customized in the software. Referring to the "Field 1" box in FIG. 4, a user can specify through the software a specific "Exact String" of characters for the barcode scanner of the blood collection device to look for to accept a barcode as an input. In this example, the "Exact String" can be the characters "=G1234" with a Field Size of 6 characters. When the barcode scanner of the blood collection device is used to scan a barcode as an input, only barcodes beginning with this "Exact String" of characters will be recognized. The remaining characters of the barcode can be customized in the other fields of the software. Referring still to FIG. 4, "Field 2" can specify that the next 5 characters (from the Field Size column) be "Numeric" characters, "Field 3" can specify that the 3 characters following "Field 2" are "Alpha" characters, and "Field 4" can specify that the final 2 characters be "Numeric" characters.

Still referring to FIG. 4, a user of the software can specify when in the blood collection process the blood collection device prompts a phlebotomist for the barcode. In this example, "Barcode No. 1" is requested at the "Start of Donation" (referring to the "When" box in FIG. 4). Furthermore, a user of the software can even customize what is displayed on the blood collection device when the specific barcode is requested for input, as shown in the "Display" box of FIG. 4. In this example, a 16 character barcode, starting with the characters "=G1234", followed by 5 numbers, followed by 3 letters, followed by 2 numbers, will be requested by the blood collection device at the start of a blood collection procedure. The blood collection device will display the words "Nurse ID" at that time in the procedure, to indicate to the nurse or phlebotomist to scan his or her employee barcode at that point in the procedure.

Figure 5:
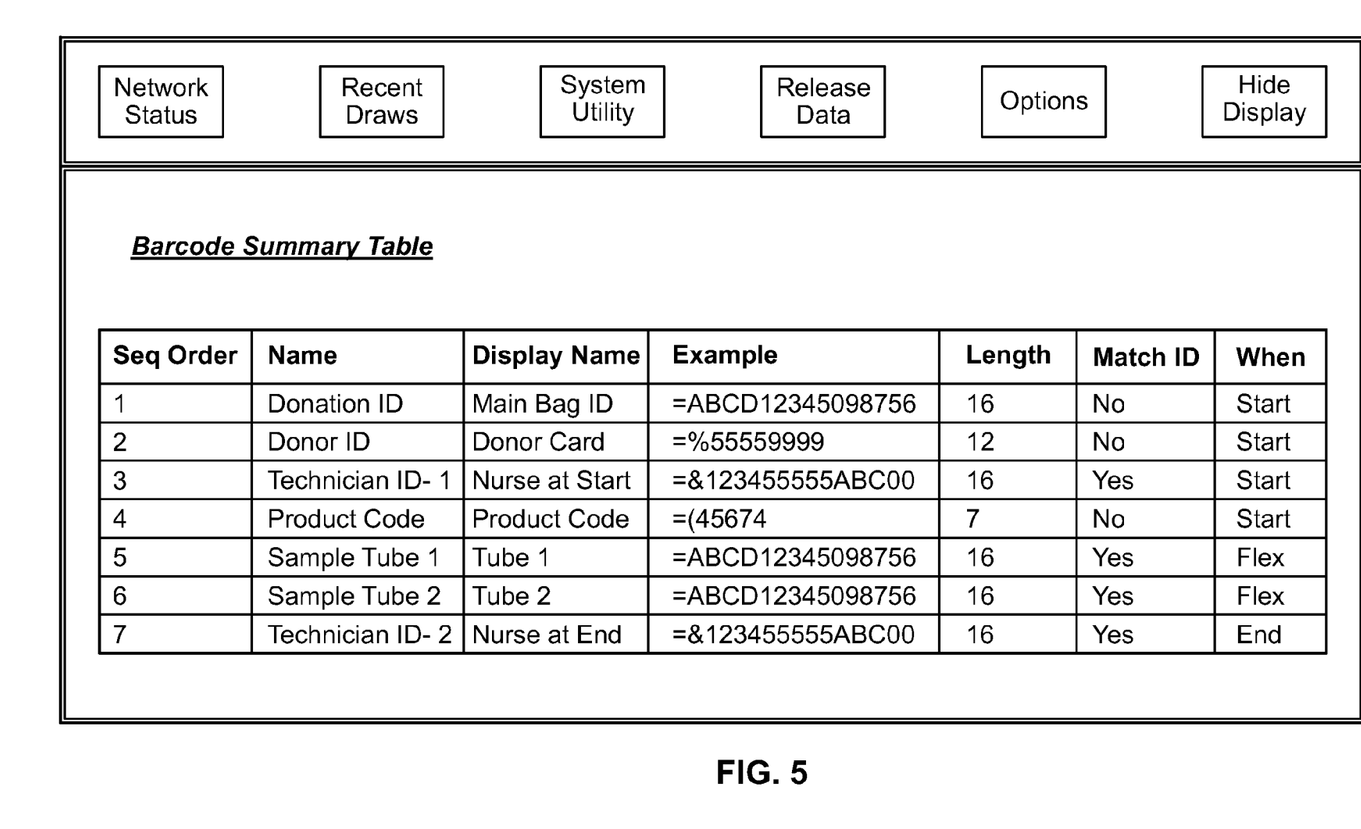

This gives the software the ability to configure many types of barcodes as inputs to the blood collection device, and also to specify what point of the procedure to scan that barcode. FIG. 5 illustrates one sequence of different types of barcodes that can be scanned at different times in a blood collection procedure. As described above, each of the barcode types, names, and times can be customized in the software system. Referring to FIG. 5, at the start of a blood collection procedure, the blood collection device can request the Donation ID barcode on a main blood bag to be scanned, followed by scanning the Donor ID barcode on a donor card, followed by scanning a Technician ID barcode of a nurse/phlebotomist, followed by scanning a Product Code of a product, such as blood. Once sequence steps 1-4 have been completed, the blood collection device will be allowed to begin the blood collection process. Next, sequence steps 5-6, of scanning the barcodes of Sample Tubes 1 and 2, will be requested during the blood collection process, prior to the end of drawing blood. Finally, after the blood draw is complete, a second Technician ID will be scanned (either the original nurse/phlebotomist or the nurse/phlebotomist monitoring the procedure at the time of completion).

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of specifying a collection protocol for a blood collection device, the method comprising:
    specifying in a blood collection control system, a first input to be scanned, the first input being selected from the group consisting of a donation ID barcode on a blood collection bag, a donor ID, a technician ID that identifies the user at a start of the blood collection event, a blood product code, a first sample tube, a second sample tube, a biometric input, and a technician ID that identifies the user at an end of the blood collection event;
    specifying in the blood collection control system, a first time during a blood collection event for the blood collection device to prompt a user to scan the first input;
    specifying in the blood collection control system, a second input to be scanned, the second input being selected from the group consisting of a donation ID barcode on a blood collection bag, a donor ID, a technician ID that identifies the user at a start of the blood collection event, a blood product code, a first sample tube, a second sample tube, a biometric input, and a technician ID that identifies the user at an end of the blood collection event;
    specifying in the blood collection control system, a second time during the blood collection event for the blood collection device to prompt the user to scan the second input;
    compiling in the blood collection control system a customized blood collection protocol operable on a blood collection device and configured to prompt the user for the first input at the first time and the second input at the second time;
    transmitting the customized blood collection protocol from the blood collection control system to one or more blood collection devices;
    initiating a blood draw from a patient with one of the blood collection devices running the customized blood collection protocol;
    prompting the user for the first input at the first time during the blood draw;
    prompting the user for the second input at the second time during the blood draw; and
    completing the blood draw from the patient.

2. The method of claim 1 wherein the specifying input steps comprise specifying length and character type requirements for the first and second inputs.

3. The method of claim 1 wherein the first time is at the beginning of a blood collection process.

4. The method of claim 1 wherein the second time is at the end of a blood collection process.

5. The method of claim 1 wherein the biometric input comprises a fingerprint.

6. The method of claim 1, further comprising transmitting blood collection data regarding the collected blood from one or more of the blood collection device to the blood collection control system.

7. The method of claim 1, further comprising:
    turning on a transmit function for each of to one or more blood collection devices and transmitting blood collection data from the blood collection devices to the blood collection control system;
    turning off the transmit function of the blood collection devices after the blood collection data is received by the blood collection control system; and
    waiting for a time interval before again turning on the transmit function of the blood collection devices.

* * * * *